United States Patent
Borgert et al.

(12) 
(10) Patent No.: US 7,400,136 B2
(45) Date of Patent: Jul. 15, 2008

(54) MULTISCALE LOCALIZATION PROCEDURE

(75) Inventors: Jörn Borgert, Hamburg (DE); Volker Rasche, Hamburg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 67 days.

(21) Appl. No.: 10/553,771

(22) PCT Filed: Apr. 14, 2004

(86) PCT No.: PCT/IB2004/001204

§ 371 (c)(1),
(2), (4) Date: Jun. 23, 2006

(87) PCT Pub. No.: WO2004/095044

PCT Pub. Date: Nov. 4, 2004

(65) Prior Publication Data
US 2006/0267579 A1    Nov. 30, 2006

(30) Foreign Application Priority Data
Apr. 22, 2003  (EP)  ................... 03101101

(51) Int. Cl.
*G01B 7/15* (2006.01)
*H01F 5/00* (2006.01)
*G01N 27/72* (2006.01)

(52) U.S. Cl. .............. 324/207.15; 324/225

(58) Field of Classification Search ........... 324/202, 324/207.12, 207.15–207.17, 207.26, 225, 324/246; 342/126; 250/201.6; 367/103; 600/424
See application file for complete search history.

(56) References Cited

U.S. PATENT DOCUMENTS

| | | | |
|---|---|---|---|
| 3,768,459 A * | 10/1973 | Cannon et al. | 600/588 |
| 4,317,078 A * | 2/1982 | Weed et al. | 324/207.26 |
| 5,711,299 A | 1/1998 | Manwaring et al. | |
| 5,729,129 A * | 3/1998 | Acker | 324/207.12 |
| 5,913,820 A | 6/1999 | Bladen et al. | |
| 2002/0058874 A1 | 5/2002 | Ono et al. | |

FOREIGN PATENT DOCUMENTS

| | | |
|---|---|---|
| EP | 1 096 268 A2 | 5/2001 |
| WO | WO 96/41119 A1 | 12/1996 |
| WO | WO 99/49783 A1 | 10/1999 |
| WO | WO 01/01685 A1 | 1/2001 |

OTHER PUBLICATIONS

Gatehouse, P.D., et al.; Tracking local volume 3D-echo-planar coronary artery imaging; 2002; IEEE; abstract.
Seiler, P.G., et al.; A novel tracking technique for the continuous precise measurement of tumour positions in conformal radiotherapy; 2000; Phys. Med. Biol.; 45:N103-N110.
Wynn, W.M., et al.; Advanced superconducting gradiometer/magnetometer arrays and a novel signal processing technique; 1975; IEEE; MAG-11(2)701-707.

* cited by examiner

*Primary Examiner*—Patrick Assouad
*Assistant Examiner*—Kenneth J Whittington

(57) ABSTRACT

Position measurements are often performed using a localization system with a given fixed capture range and accuracy and resolution. Having a fixed capture range often comes at the cost of decreased accuracy and resolution. At the start, a large capture range is provided where the accuracy and resolution is low. In this large capture area, the target area can be identified and aimed at. With this identification, a smaller capture range is iteratively provided and centered around the region of interest, which leads to an increased accuracy and resolution.

17 Claims, 5 Drawing Sheets

MULTISCALE LOCALIZATION PROCEDURE

BACKGROUND

The present invention relates generally to position and/or orientation measurements. In particular, the present invention relates to a tracking method for tracking a sensor in a capture range in a field generated by a field generator, a tracking system for tracking a sensor in a capture range in a field generated by a field generator and to a computer program product comprising computer program code means.

Known systems for performing position measurements use a localization system with a given fixed capture range and accuracy and resolution. Having a fixed size and desirably large capture range often comes at the cost of decreased accuracy in resolution. This bears two problems: either the capture range or the accuracy and resolution do not match the needs of a user.

P. G. Seiler et al: "A novel tracking technique for the continuous precise measurement of tumour positions in conformal radiotherapy" Phys. Med. Biol. 45 (2000) N103-N110 describes a tracking technique using magnetic fields as information carriers between a field generator and a field sensor, similar to other magnetic tracking applications such as Wynn et al "Advanced superconducting gradiometer/magnetometer arrays and a novel signal processing technique" IEEE Trans. Magn. 11 701-7. However, the capture range defined by the field generated with the field generator remains the same for all applications and measurements.

SUMMARY

It is an object of the present invention to provide for a localization and tracking of a sensor with a high accuracy and resolution.

According to an exemplary embodiment, this object may be solved with a tracking method for tracking a sensor in a capture range in a field generated by a field generator, wherein a field is generated by means of the field generator for defining the capture range, a region of interest including the sensor is identified within the capture range and the capture range is iteratively narrowed by narrowing the field by means of a field generator to enclose the region of interest.

In other words, the localization and tracking according to this exemplary embodiment of the present invention starts at a coarse level, where the region of interest is identified and navigated to. In the following iterative process, the capture range of the localization and tracking system is narrowed step by step and the accuracy and precision is thus increased. During each step, the region of interest may be subject to measurement of the position with increasing accuracy and precision and a high and steady-going frame rate of acquisition, because the system has to track only one target at a time. The tracking of a plurality of targets often results in a smaller frame rate. Within this application, the term "to narrow" is to be interpreted as including any adjustment with respect to at least one of a size, direction and orientation of the capture range to achieve an adjustment, shifting and/or moving of the capture range. The iteration ends, when the position measurement can be performed at the desired level of accuracy and resolution, either given by the user or the limitations of the system.

According to other exemplary embodiments, a position of at least one coil in the field generator is adjusted, the field generator itself is adjusted or an orientation of at least one coil in the field generator is adjusted for narrowing the capture range. According to these exemplary embodiments, a very simple and effective method for narrowing the capture range is provided, which allows to adjust the capture range with a high degree of accuracy.

Preferably, the method is supported by a "scalable localization system" which can be scaled in terms of the size and position of the box of motion or capture range and the accuracy and resolution.

According to another exemplary embodiment, a tracking system is provided for tracking a sensor in a capture range in a field generated by a field generator, wherein the field generator is adapted to adjust one of a size, direction and orientation of the capture range. Advantageously, the tracking system according to the exemplary embodiment of the present invention allows to meet with an accuracy and resolution required by a user for different applications.

As set forth in the exemplary embodiments, the capture range may be adjusted by adjusting a position of at least one coil in the field generator, by adapting the field generator such that it is moveable and by accordingly moving the field generator or by adjusting an orientation of at least one coil in the field generator. Alternatively, a plurality of coil arrangements may be provided, each generating a different size of field, i.e. capture range, which can be iteratively selected.

According to another exemplary embodiment, a computer program product is provided comprising computer program code means to perform the method according to the present invention when the computer program is executed on a computerized tracking system. Advantageously, the computer program product according to the present invention allows to minimize a computational power required in the tracking system by providing an iterative procedure which can easily be performed.

The capture range is iteratively adjusted to a level where the accuracy and resolution required in a certain application is met. When the capture range is large, the required accuracy and resolution is low. So, the target area can be identified and aimed at. Given this identification, the capture range can be focused and centered around the region of interest, which in turn leads to increased accuracy, resolution and frame rate. This process can be repeated in iterations leading to a small capture range and a large accuracy and resolution.

These and other aspects of the present invention will become apparent from and elucidated with reference to the embodiments described hereinafter.

Exemplary embodiments of the present invention will be described in the following with reference to the following drawings:

DETAILED DESCRIPTION

Figure 1:
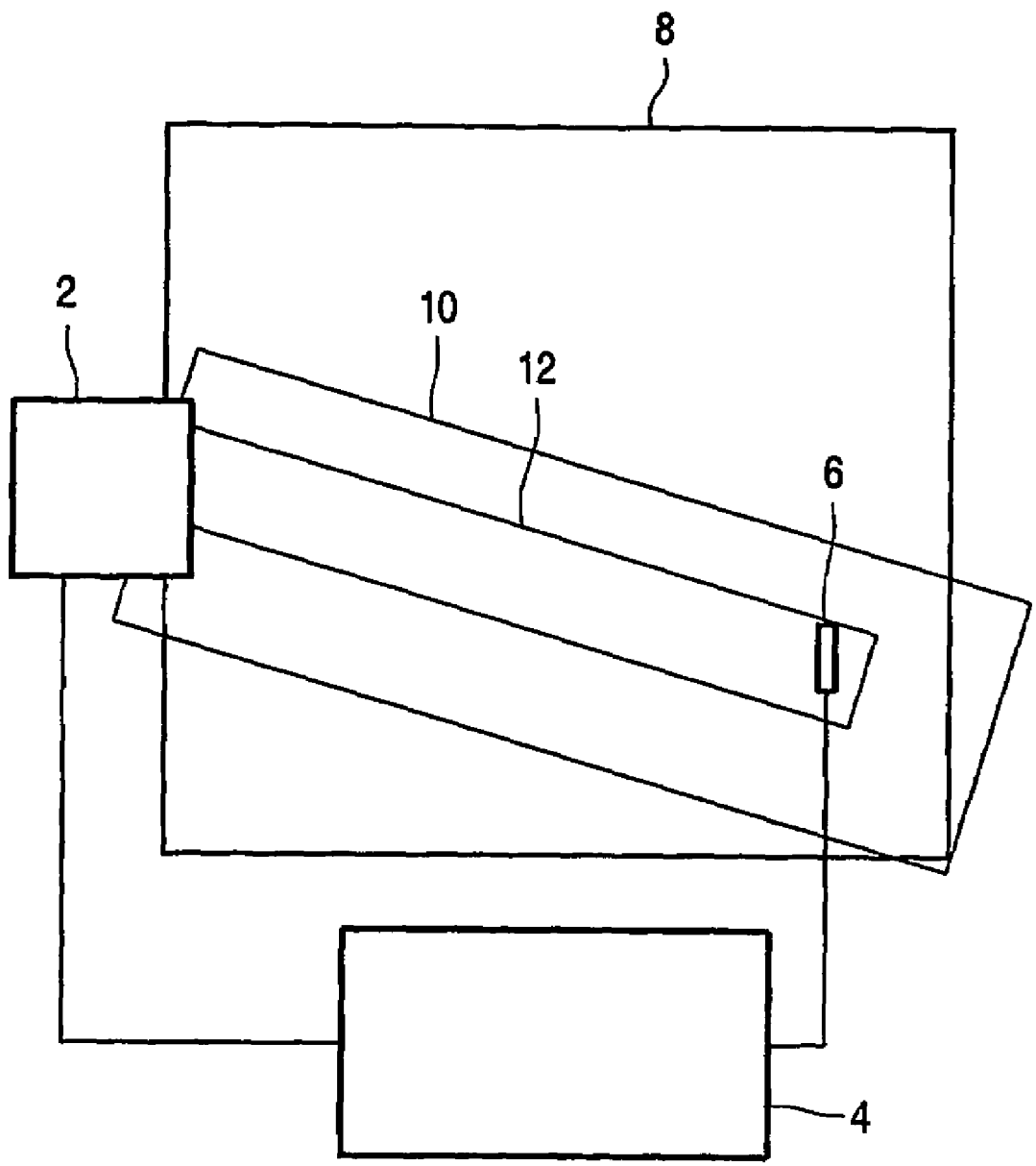
FIG. 1 shows a schematic representation of a localization and tracking system according to an exemplary embodiment of the present invention.

FIG. 1 shows an exemplary embodiment of a localization and tracking system according to the present invention. Reference character 2 designates a field generator which is connected to a calculation unit 4. The calculation unit 4 is connected to a sensor 6. The calculation unit 4 is adapted to control the field generator 2 such that it generates fields with capture ranges of a different size. Reference character 8 designates a capture range generated by the field generator 2 for identifying the target area, namely the location of the sensor 6 and to aim at. Then, the calculation unit 4 controls the field generator 2 such that it generates a narrowed field with a narrowed capture range 10, which includes the region of interest, namely the sensor 6. Since the capture range 10 is more focused than the capture range 8, the accuracy and resolution in the capture range 10 is higher than in the capture range 8. Then, the calculation unit 4 controls the field generator 2 such that it generates a field for a further capture range 12, including the sensor 6. Since the capture range 12 is more focused than the capture range 10, the accuracy and resolution provided within the capture range 12 is better than in the capture range 10.

In the following exemplary embodiments of the field generator 2, the calculation unit 4 and the sensor 6 will be described in her detail.

The field generator 2 is preferably a magnetic field generator and may comprise six differential coils, which form the edges of the tetrahedron shaped assembly. Each differential coil comprises two coils of opposite polarization, which are positioned behind each other on the same axis. Therefore, during a half period of an alternating field, a magnetic pole array generated by the coils is varied from S-N-N-S to N-S-S-N, S meaning south pole and N meaning north pole. Such a coil arrangement creates a multipole field with a dominant quadrupole component. Each coil contains 83 windings of copper wire wound on a core made of synthetic material. The differential coils are assembled by means of interconnecting plastic pieces to form a tetrahedron with an edge length of approximately 16 cm.

As sensor 6, a miniaturized induction coil may be used. Such a coil may consist of 1000 windings of insulated copper wire having a diameter of 20 μm wound on a piece of soft iron. By this, a sensor may be manufactured having outer dimensions of 8 mm×0.8 mm diameter. Preferably a coating is provided consisting of a thin film of synthetic material. The alternating magnetic field created by the field generator 2 induces an alternating voltage in the sensor, which is measured by the calculation unit connected to the sensor 6.

The coils of the field generator 2 are excited one after the other during a measurement cycle by an alternating current of ±2 A at 12 kHz for 3.3 ms each. Thus, one measurement cycle requires approximately 10 ms. During each cycle, the corresponding induction voltages determined by the sensor 6 are measured and evaluated by the calculation unit 4.

Using six induction voltages induced in the sensor by the six differential coils of the field generator 2, three Cartesian coordinates and two angles may be identified.

An algorithm to calculate the position of the sensor 6 within the space of the capture range may be taken from Seiler et al "A novel tracking technique for the continuous precise measurement of tumor positions in conformal radiotherapy", Phys. Med. Biol. 45 (2002) N103-N110, which is hereby incorporated by reference. The calculation unit 4 may comprise a digital signal processor (DSP) and a digital to analog converter (DAC). Furthermore, the calculation unit 4 comprises a localizer system.

Figure 2C:
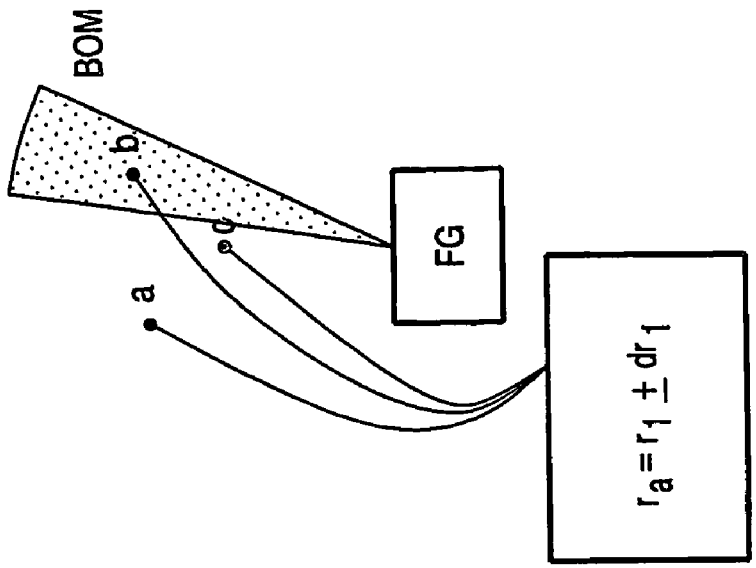
FIGS. 2a to 2c are illustrations depicting an operation of the localization and tracking system of FIG. 1.
Figure 2B:
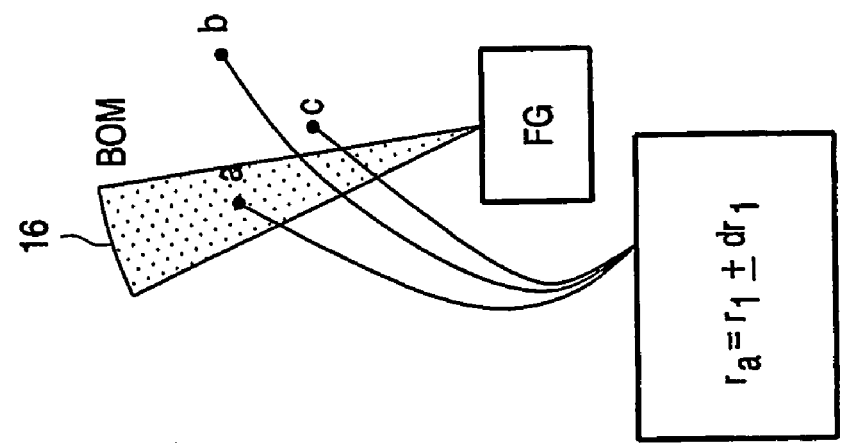
Figure 2A:
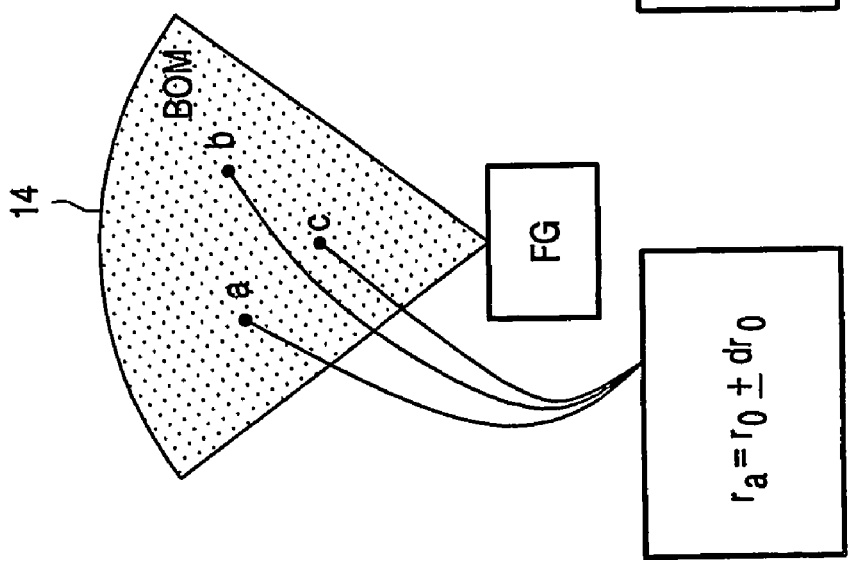

FIGS. 2a to 2c are illustrations for further explaining an operation according to an exemplary embodiment of the present invention of the localization and tracking system of FIG. 1 with respect to a position measurement. Normally, as shown in FIG. 2a, the system is built to ensure a given accuracy and resolution in a given box of motion (BOM). In other words, the field generator FG is controlled such that it generates a given capture range 14. However, the given accuracy and resolution is not sufficient for all applications. According to the present invention, this limitation is bypassed by providing the possibility to adjust the trade-off between the size/dimension of the BOM and the accuracy and resolution during the tracking and/or localization procedure.

At the start of the method, the BOM or capture range 14 is large. In this capture range 14, the accuracy and resolution is low. At this stage shown in FIG. 2a, the position of other parameters to be determined by the system can be given only on a very coarse scale: $r_a = r_0 \pm dr_0$. However, here, the regions of interest, namely a, b, and c, can easily be identified. Then, as depicted in FIG. 2b, with the knowledge of the region of interest to be localized, here region a, the BOM can be adjusted to the capture range 16. As obvious from FIGS. 2a and 2b, the capture range 16 is more focused than the capture range 14.

The position and size of the capture range 16 is controlled such that it is centered around the region of interest a. Since the capture range 16 was more focused, measurements having a higher accuracy and better resolutions are possible: $r_a = r_1 \pm dr_1$ with $dr_1 < dr_0$ (where $dr_0$ and $dr_1$ are uncertainties in position). Due to the capture range having a reduced size, a higher frame rate of acquisition is possible because the system has to track only one target, namely the region of interest at one time and not all three targets a, b and c at the same time. This centering of the capture range and reducing the size of the capture range can be iterated to provide an even higher accuracy and precision with a stepwise smaller box of motion and capture range until the desired accuracy and resolution or the highest possible accuracy and resolution of the system are reached.

As shown in FIG. 2c, it is possible to measure parameters of all regions of interest (a, b and c) inside the capture range 14 at the coarse scale. These parameters, including for example a position, a speed, a direction of movement are saved in the calculation unit 4.

If, after a refinement of the capture range or BOM with respect to one region of interest, another region of interest lies outside the BOM, such as region of interest b in FIG. 2b, the saved parameters about that region of interest can be used to refine the BOM/capture range around that entity. Due to this, the system is capable of switching between all localizable regions of interest (a, b and c) to provide localization and tracking information with the highest accuracy and resolution possible.

If it happens that a moving target escapes a box of motion and thus cannot be tracked any more, the system can be switched back to a larger box of motion. Having done this, the capture range is enlarged and thus the target can again be aimed at, centered to and tracked.

Figure 3:
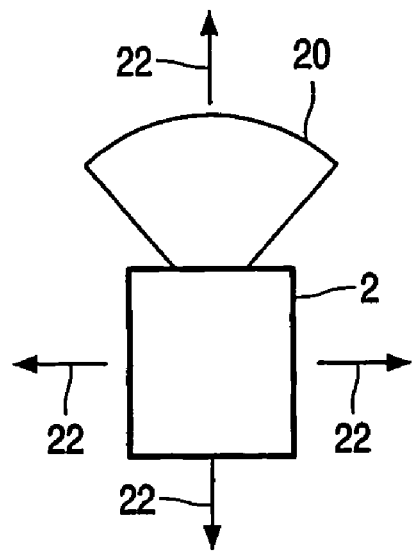
FIG. 3 is a schematic representation of a field generator according to the present invention as it may be used in the localization and tracking system of FIG. 1.

FIG. 3 shows an exemplary embodiment of a field generator 2 according to the present invention, as it may be used in the localization and tracking system of FIG. 1. The field generator 2 generates a magnetic field corresponding to a capture range 20. As depicted with arrows 22 in FIG. 3, the field generator 2 is moveable. By moving the field generator, which means by changing its position in relation to the environment, an orientation and a position of the capture range 20 can be adjusted. The field generator 2 may be moved by means of electric actuators (not depicted in FIG. 3). However, the field generator 2 may be mounted to a rail system and manipulated manually.

Figure 4:
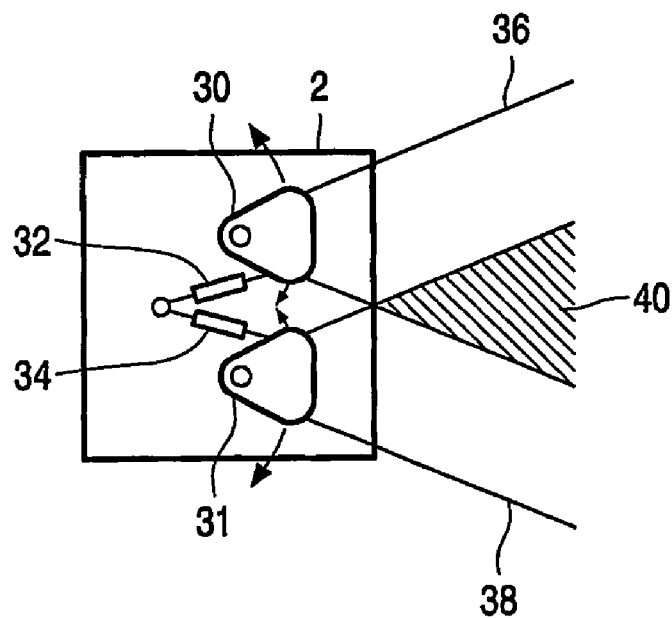
FIG. 4 shows a schematic representation of an exemplary embodiment of a field generator according to the present invention as it may be used in the localization and tracking system of FIG. 1.

FIG. 4 shows another exemplary embodiment of a field generator 2 as it may be used in the localization and tracking system of FIG. 1 according to the present invention. The field generator 2 depicted in FIG. 4 comprises two emitters or coils 30 and 31. The emitters or coils 30 and 31 are arranged in the field generator 2 such that an orientation and/or position of the emitters or coils 30 and 31 can be changed or manipulated by means of actuators 32 and 34. Each of the emitters or coils 30 and 31 emits a beam 36 or 38. According to this exemplary embodiment of the present invention, by adjusting the positions and/or orientations of the emitter or coils 30 and 31, orientations and positions of the beams 36 and 38 can be adjusted, whereby a size and/or orientation of the capture range of BOM 40 can be adjusted. Alternatively, different sets of coils 30 and 31 may be provided, each set having a different direction and orientation, whereby different capture ranges 40 are provided. Then, by selecting the respective sets of coils, a desired capture range may be selected. Also, an adaptive coil configuration may be used.

Figure 5:
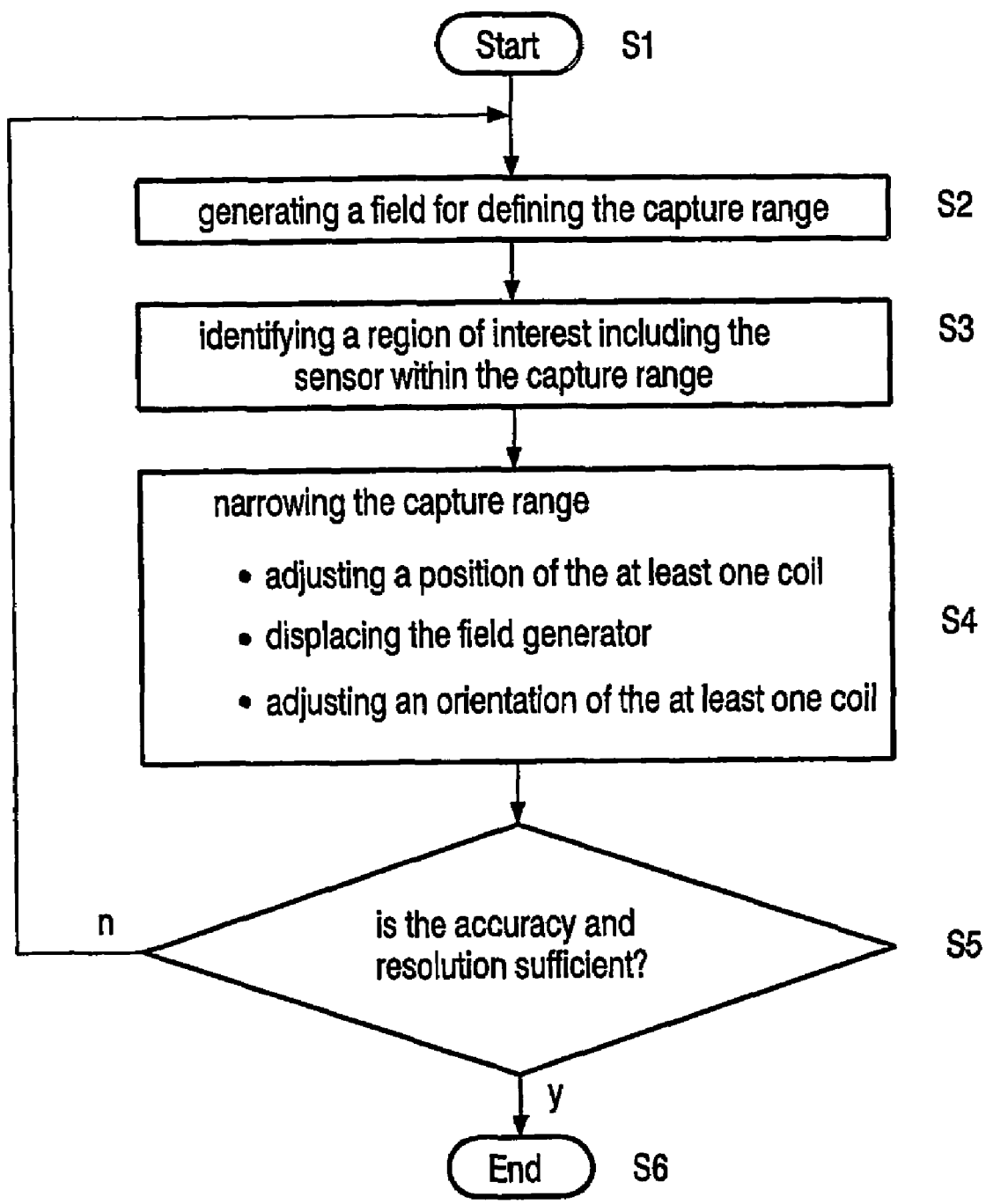
FIG. 5 is a flow-chart of an exemplary embodiment of a method for operating the localization and tracking system of FIG. 1 according to the present invention.

FIG. 5 shows an exemplary embodiment of a method of operating the localization and tracking system of FIG. 1 according to the present invention. After the start in step S1, the method continues to step S2 where, by means of the field generator 2, a magnetic field is generated which defines the capture range 8. As indicated above, the capture range 8 is large and allows to localize the region of interest with the sensor 6 only on a very coarse level. Then, in the subsequent step S3, the region of interest, including the sensor 6 is identified within the capture range 8. In case of more than one sensor, the sensor to be tracked has to be selected manually or by suitable automatic means; e.g. selecting the sensor closest to a given anatomical structure. Then, the method continues to S4, where the capture range is narrowed. The capture range is narrowed such that the region of interest identified in step S3 is in the center of the capture range with the reduced size. As indicated in FIG. 1, in step S4 the capture range is reduced from the capture range 8 to the capture range 10. The capture range may be narrowed by either adjusting a position of the at least one emitter/coil in the field generator 2, displacing the field generator 2 or by adjusting an orientation of the at least one emitter/coil in the field generator 2. Then, in the subsequent step S5, a query is made, whether the accuracy and resolution provided within the capture range 10 is sufficient. In case it is determined by an operator or by a comparison to a pre-set threshold value that the accuracy and resolution is not sufficient, the method iteratively goes back to step S2 where a field corresponding to the reduced capture range is generated. Then, in step S3, the region of interest including the sensor 6 is identified 20 within the capture range 10. Then, in the subsequent step S4, the capture range is narrowed to the capture range 12. In case the accuracy and resolution is sufficient, the method continues from step S5 to step S6, where it ends.

Figure 6A:
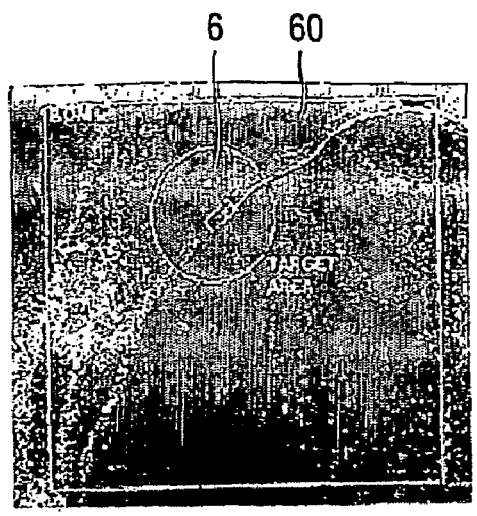
FIGS. 6a to 6c are a visualization of the iterative multiscale localization and tracking system in accordance with the present invention.
Figure 6B:
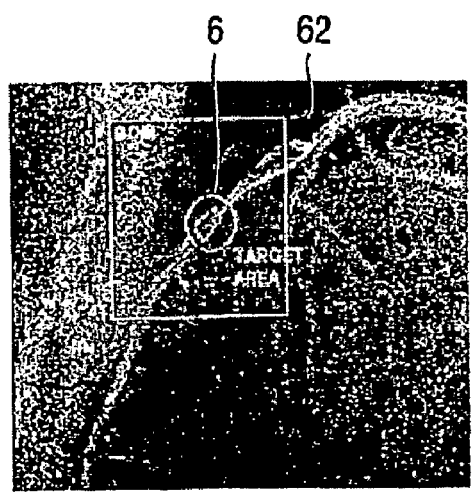
Figure 6C:
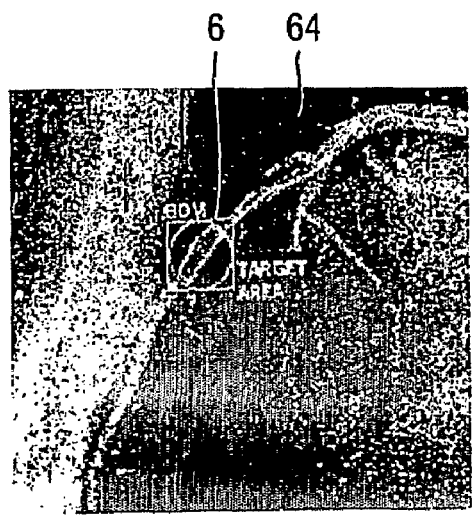

FIGS. 6a to 6c show a visualization of the iterative multi-scale localization and tracking procedure according to the present invention. In the example of FIGS. 6a-6c, a catheter including a sensor is inserted into an artery. The capture range or BOM, which is two-dimensional in FIGS. 6a to 6c, but which can also be one or three dimensional, is relatively large, such that the sensor 6 can be identified, but a localization is only possible with a limited accuracy. Then, in FIG. 6b, a smaller capture range 62 allows for a more accurate localization and tracking of the sensor 6.

As can be taken from FIG. 6c, an even smaller capture range 64 is provided, allowing for a very accurate localization and tracking of the sensor 6.

The present invention may advantageously be applied in applications which are given by the localization, tracking and navigation in a catheter laboratory, where the navigation aids a physician in the placement of interventional devices such as catheters, balloons or stents. Also, advantageously, the present invention may be applied in coronary applications or during other procedures such as electro-physiology (EP). Advantageously, by applying the present invention, x-ray imaging of devices with virtual position information can be omitted, which allows to decrease an x-ray dose applied to the patient. However, the present invention may also be applied in other applications such as in fields of a targeted drug delivery in the context of molecular imaging where the local administration of medicine or drugs is a fundamental part of the process.

The invention has been described with reference to the preferred embodiments. Modifications and alterations may occur to others upon reading and understandting the preceding detailed description. It is intended that the invention be construed as including all such modifications and alterations insofar as they come within the scope of the appended claims or the equivalents thereof.

The invention claimed is:

1. A tracking method for tracking a sensor in a capture range in a field generated by a field generator, the method comprising the steps of:
   (a) generating a field by means of the field generator for defining the capture range;
   (b) identifying a region of interest including the sensor within the capture range based on a signal from the sensor;
   (c) adjusting at least one of size, direction and orientation of the capture range to a level where the sensor is located with an iteratively improved accuracy and resolution until a preselected accuracy and resolution are achieved;
   (d) narrowing, focusing and centering the capture range by narrowing the field by means of the field generator;
   (e) iteratively repeating steps (a) to (d).

2. The method of claim 1, wherein the field generator is a magnetic field generator and emits a magnetic field, wherein the magnetic field generator comprises at least one coil, further comprising the step of: adjusting a position of the at least one coil in the field generator for narrowing the capture range such that at least one of a size and shape of the capture range is reduced.

3. The method of claim 1, further comprising the step of displacing the field generator for narrowing the capture range.

4. The method of claim 1, wherein the field generator is a magnetic field generator and emits a magnetic field, wherein the magnetic field generator comprises at least one coil, further comprising the step of: adjusting an orientation of the at least one coil in the field generator for narrowing the capture range such that a location of the capture range is adjusted.

5. The method of claim 1, wherein the sensor includes:
   a miniaturized induction coil;
   outer dimensions of about 8 mm by 0.8 mm diameter; and
   a thin film of synthetic material coating.

6. The method of claim 1, further including the step of determining between steps (d) and (e) whether the accuracy and resolution provided within the capture range meets a preselected threshold.

7. The method of claim 1, wherein step (d) further includes improving a resolution with which the region of interest is identified as the capture ratio is narrowed.

8. A tracking system for tracking a sensor in a capture range in a field generated by a field generator, wherein:
   the field generator iteratively adjusts at least one of a size, direction and orientation of the capture range to a level where the sensor is located with an iteratively improved accuracy and resolution until a preselected accuracy and resolution are achieved; and
   the field generator focuses, narrows, and centers the capture range to be focused on a region of interest based on a signal from the sensor.

9. The tracking system of claim 8, wherein the field generator is a magnetic field generator and emits a magnetic field; wherein the magnetic field generator comprises at least one coil; and wherein a position of the at least one coil in the field generator is adjustable for narrowing the capture range such that at least one of a size and shape of the capture range is reduced.

10. The tracking system of claim 8, wherein the field generator is movable for narrowing the capture range.

11. The tracking system of claim 8, wherein the field generator is a magnetic field generator and emits a magnetic field; wherein the magnetic field generator comprises at least one coil; and wherein an orientation of the at least one coil in the field generator is adjustable for narrowing the capture range such that a location of the capture range is adjusted.

12. The tracking system of claim 8, wherein the field generator includes:
   a plurality of differential coil assemblies, each differential coil assembly including a pair of opposite polarity coils with a common axis.

13. The tracking system of claim 12, wherein the sensor includes:
   an induction coil coated with a thin film of synthetic material.

14. The tracking system of claim 8, wherein the field generator includes:
   a first coil mounted to pivot about a first axis;
   a second coil mounted to pivot about a second axis, the second axis being parallel to the first;
   a plurality of actuators which rotate the first and second coils about the first and second axes, respectively;
   a control which controls the acutators to adjust an amount of rotation of the first and second coils to focus, center, and narrow the capture range.

15. The tracking system of claim 8, wherein the field generator is a magnetic field generator and emits a magnetic filed, the field generator including: two coils each mounted for rotation relative to a corresponding spaced axis; and,
   actuators which rotate each of the coils relative to the corresponding axis.

16. A tracking method for tracking a sensor in a capture range in a field generated by a field generator, the method comprising the steps of:
   (a) generated a field by means of the field generator for defining the capture range;
   (b) identifying a region of interest including the sensor within the capture range;
   (c) narrowing the capture range by narrowing the field by means of the field generator;
   (d) iteratively repeating steps (a) to (c);
   wherein the field generator is a magnetic field generator and emits a magnetic filed, the field generator including: two coils each mounted for rotation relative to a corresponding spaced axis; and,
   actuators which rotate each of the coils relative to the corresponding axis.

17. A computer program product comprising computer program code means to perform the following steps when the computer program is executed on a computerized tracking system:
   (a) generating a field by means of the field generator for defining the capture range;
   (b) identifying a region of interest including the sensor within the capture range based on a signal from the sensor;
   (c) narrowing and focusing the capture range by narrowing the field by means of the field generator to the region of interest and improving a resolution with which a location of the region of interest can be resolved;
   (d) iteratively repeating steps (a) to (c) until the location of the region of interest is resolved with a selected resolution.

* * * * *